United States Patent [19]

Miyajima

[11] Patent Number: 5,005,420

[45] Date of Patent: Apr. 9, 1991

[54] ULTRASONIC METHOD FOR MEASUREMENT OF DEPTH OF SURFACE OPENING FLAW IN SOLID MASS

[75] Inventor: Takeshi Miyajima, Ibaraki, Japan

[73] Assignee: Hitachi Construction Machinery Co., Ltd., Tokyo, Japan

[21] Appl. No.: 381,684

[22] PCT Filed: Jun. 8, 1987

[86] PCT No.: PCT/JP87/00358

§ 371 Date: Mar. 30, 1989

§ 102(e) Date: Mar. 30, 1989

[87] PCT Pub. No.: WO88/09931

PCT Pub. Date: Dec. 15, 1988

[51] Int. Cl.$^5$ .............................................. G01N 29/04
[52] U.S. Cl. ........................................ 73/629; 73/620
[58] Field of Search ................. 73/602, 618, 620, 629, 73/633

[56] References Cited

U.S. PATENT DOCUMENTS

| | | | |
|---|---|---|---|
| 3,776,026 | 12/1973 | Adler et al. | 73/602 |
| 4,274,288 | 6/1981 | Tittmann et al. | 73/602 |
| 4,759,221 | 7/1988 | Ortlieb et al. | 73/602 |
| 4,785,667 | 11/1988 | Miyajima et al. | 73/618 |

*Primary Examiner*—John Chapman
*Assistant Examiner*—Louis M. Arana
*Attorney, Agent, or Firm*—Wenderoth, Lind & Ponack

[57] ABSTRACT

The present invention provides a method for ultrasonic measurement of mainly the depth of a flaw possibly existent in a solid mass and opening to the surface of the solid mass. An ultrasonic wave is transmitted into the solid mass by scanning an ultrasonic probe back and forth on the surface of the solid mass with respect to a flaw in the solid mass, a threshold of a predetermined level is set for a curve defined by levels of echoes of the ultrasonic waves reflected from the flaw according to the position of probe, the area under the curve and above the threshold is integrated for the range of movement of the probe, and the depth of the surface opening flaw is measured using as an evaluation index the value of the integrated area of the area. The method according to the present invention is applicable to nondestructive, easy, accurate and realtime measurement of the depth of weld cracking in a welded portion, fatigue cracks in a stress-concentrated portion of members of a machine, etc.

4 Claims, 12 Drawing Sheets

MOVED DISTANCE OF THE PROBE

ULTRASONIC METHOD FOR MEASUREMENT OF DEPTH OF SURFACE OPENING FLAW IN SOLID MASS

TECHNICAL FIELD

The present invention relates to an ultrasonic method for measurement of the depth of any surface opening flaw possibly existent in a solid mass.

The term "surface opening flaw" in a solid mass used herein refers not only to a flaw developed as an opening on the surface of parts or members of whatever the height, composing, for example, electrical, mechanical equipment or installations, etc. in various industrial fields, but to a flaw not actually opening but existent very closely to the surface. More particularly, the surface opening flaws or open-on-surface flaws include a variety of cracks such as weld cracking in a welded portion, quench cracks caused during a heat treatment, grinding cracks produced during grinding, stress corrosion cracking, etc. and fatigue cracks, etc. in materials, to all of which the present invention is applicable. Also, the term "solid mass" described herein refers to a mass of a metal as well as a mass of a nonmetal such as glass, ceramics, synthetic resin, rubber, etc. through which ultrasonic waves can be propagated.

The "depth of surface opening flaw" as used herein means the vertical distance from the surface of a solid mass from which the flaw opens to the end of the depth in the solid mass.

BACKGROUND ART

For an ultrasonic measurement of the depth of a flaw opened on the surface of a solid mass, such as weld cracking in a welded portion, a fatigue crack in a member portion in which stresses concentrate, etc., various methods have recently been studied because of the necessity for the measured information, and the results from the studies have been reported. For example, (1) the measurement of the fatigue-crack depth by the end peak echo method is reported in the "Nondestructive Inspection" Vol. 31, No. 9, September, 1982, pp. 690-691, (2) a method for inspection for cracks using scattered ultrasonic waves is disclosed in the "Nondestructive Inspection" Vol. 29, No. 2, February, 1980, pp. 136-137, (3) the measurement of the height of incomplete penetration in a welded portion of steel plates is disclosed in the "Non-destructive Inspection" Vol. 34, No. 2, February, 1985, pp. 112-113, and (4) the accuracy of measurement of the notch depth based on time lapse of ultrasonic wave is described in the "Non-destructive Inspection" Vol. 29, No. 2, February, 1980, pp. 130-131.

In the measurement disclosed in the report (1), a spot-focusing type longitudinal wave angle probe is used to measure the relation between the beam path and various kinds of depth of slits formed axially in the inner wall of the bend of a pipe from the outer circumference of the pipe by the end peak echo method, thereby determining the crack depth from a calibration curve prepared based on the measured beam path. In the method for crack measurement using scattered ultrasonic waves in the above report (2), a probe is used which has arrayed therein an ultrasound transmitting transducer and a receiving transducer arrayed symmetrically with respect to a partition sheet. When ultrasonic waves are radiated from the transmitting transducer toward an object immersed in water, and a difference in time $\Delta t$ of the reception of scattered waves by the receiving transducer between when the object has a flaw when the object has no flaw is measured. Utilizing the correlation between the time difference $\Delta t$ and the flaw depth d, the flaw depth d is determined. In the method described in the above report (3), a two-transducer vertical-type probe is used and placed on the one-side butt joint of a plate finished smooth and having a thickness t (9 to 12 mm in the report). The depth of penetration d in the welded portion is directly read from the time base of the ultrasonic flaw detector and compared with the plate thickness, thereby measuring the height of incomplete penetration $h = (t-d)$. In the method disclosed in the above report (4), an ultrasonic flaw detector permitting measurement of the time of ultrasound propagation with a high accuracy is used to determine the notch depth based on the propagation time measured by any of the end peak echo method, short-pulsed shear wave method or surface wave method. Among the methods disclosed in these reports, the method in the report (1) needs to detect the position of the peak echo from the end of the fatigue crack. The method in the report (2) necessitates the detection of the rise time of the waveform of the received scattered wave. Also, the method in the report (3) requires the detection of echoes from an incomplete penetration and positions of the echoes on the time base, which are displayed on the ultrasonic flaw detector. More particularly, the method in the report (2) is a method in which the measurement is done using a water bath in which the object is immersed and the probe must be placed just above the surface opening flaw in the object. Thus, this method can be applied to a limited range of objects. The method in the report (3) is done with the transducer placed directly on the object and is applicable to a limited range of objects as described with the method in the report (2). In the method disclosed in the report (4), the end peak echo method and short-pulsed shear wave method necessitate the detection of the positions of the peak echoes as in the method in the report (1), and the surface wave method needs the detection of the displayed positions of echoes on the CRT screen because the depth of the notch is to be determined from the propagation time of the surface wave. Thus, in all the methods disclosed in the reports (1) thru (4), it is necessary to detect the echoes from the surface opening flaw and the positions of appearance of echoes, and the accuracy of the measurement depends upon the accuracy of this detection.

Figure 11:
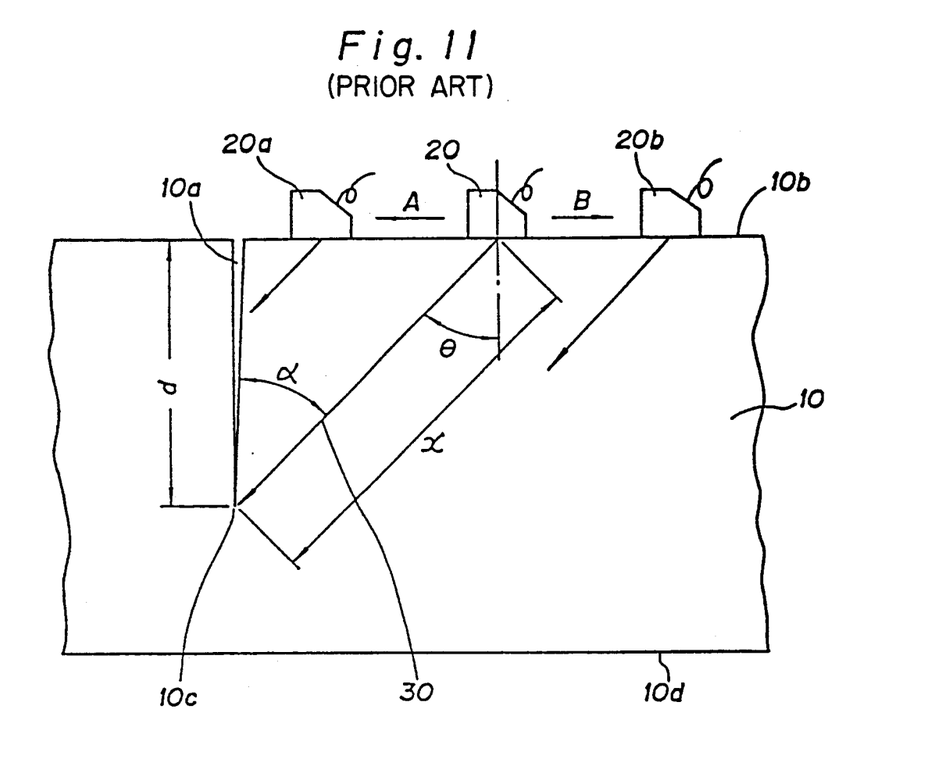
Figure 12:
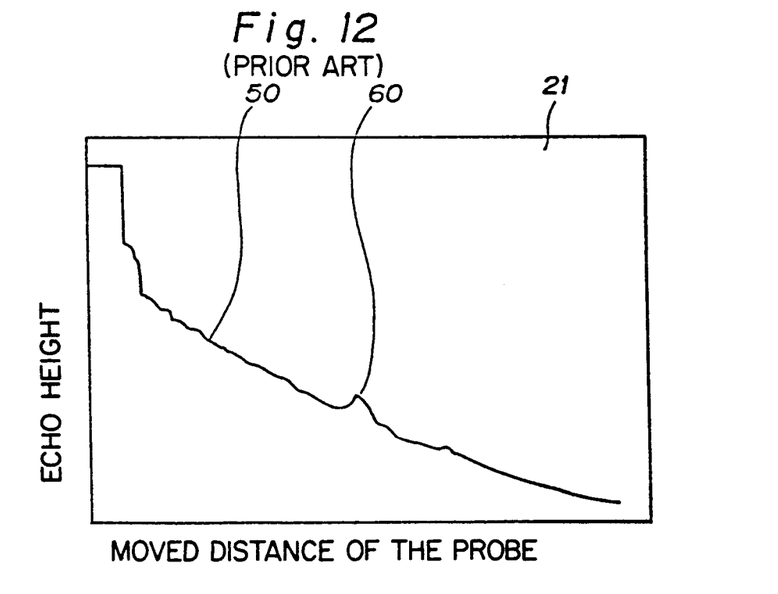

Among the above-mentioned methods, the end peak echo method is generally regarded as the most popular one. A method of measuring the depth of a surface opening flaw using this method is described in the "Ultrasonic flaw-detecting test B" - Japan Nondestructive Inspection Association (1978), pp. 117 to 118. The method of measuring under consideration will be outlined with reference to FIGS. 11 and 12. In these Figures, the reference numeral 10 indicates an object under measurement in which a planar flaw 10a is intentionally formed which has a depth d and opens on the surface of the object. The reference numeral 10b indicates a searching surface of the object 10, 10c indicates the end of the flaw 10a and 10d indicates the bottom (opposite to the searching surface 10) of the object 10. The reference numeral 20 indicates an ordinary angle probe or spot-focusing angle probe (which will be referred to as "angle probe" hereinafter). The angle probe 20 is placed in contact with the searching surface 10b, and transmits ultrasonic waves while being scanned back and forth in the direction of arrow A or B so as to pick up the echoes from the end 10c of the flaw. The reference numerals 20a and 20b indicate the selected positions of the angle probe 20 when scanned back and forth in relation to the flaw. Assume here that the angle probe 20 is scanned in the direction of arrow B from the position 20a. The echo level from the flaw 10a is displayed as continuously changed so as to gradually be lower as the angle probe 20 is moved away from the position 20a, thereby resulting in an echo envelope 50. In this case, when the beam center 30 from the angle probe 20 is incident upon the end 10c of the flaw, some peak echo 60 is displayed in a position on the CRT screen corresponding to the beam path x and the position is indicated on the echo envelope 50. The end peak echo method is such that the depth d of flaw is determined geometrically as $d = x \cdot \cos \theta$ from the beam path x of the peak echo 60 from the end 10c of the flaw and the refraction angle $\theta$ of the ultrasonic beam from the angle probe 20. In the report (1), it is described that under the conditions that the angle $\theta$ formed between the incident direction of the ultrasonic wave and the plane of the flaw 10a is more than 10 deg., an ordinary angle probe of 45 deg. in refraction angle, a spot-focusing angle probe which can limit the acoustic waves or a split-type probe should preferably be used for more definite discrimination of the peak echo 60. It is further described in the report that if the depth d of the flaw is relatively large, the depth d can be estimated with an accuracy on the order of $+/-2$ mm. However, the report also reads that in case any other flaw exists at the end 10c of the flaw, the accuracy of measurement is lower.

Figure 13A:
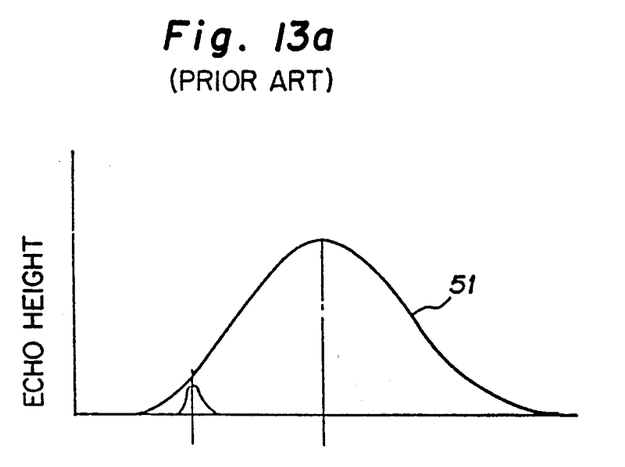
Figure 13B:
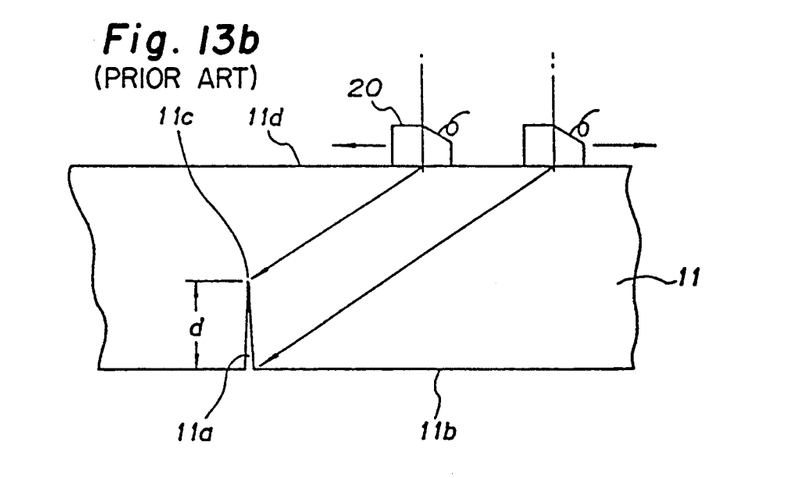

FIG. 13 shows another example of measurement by the above-mentioned end peak echo method. In this example, the angle probe 20 is placed on the surface 11a of the object in which the flaw 11a is not existent. In an echo envelope obtained in this case, the echo from the surface opening of the flaw 11a (corner echo) shows the highest peak. However, in case the depth h of the flaw 11a is small, for example, 2 mm or so, the echo from the end 11c of the flaw 11a is at so low a level as to be displayed inside the echo envelope 51 as shown in FIG. 13, and it cannot be detected in such a case. Hence, the measurement by the end peak echo method known as the most popular method for detection of surface opening flaw is disadvantageous in various aspects of the measurement as will be described below. That is, (i) When the depth d of the surface opening flaw is small, the echo from the end of the flaw is so close to the echo from any other portion of the flaw that its level and position cannot be easily distinguished from whose of the latter echo, and also the echo itself is included within an echo envelope having the corner echo as the highest value so that it cannot be detected, and at the same time since the angle probe cannot be moved over a short distance, the error of measurement is apt to be large. (ii) If the width of the flaw end is small, the level of the echo from the flaw end is small and less than the echo level at the noise level so that the echo itself cannot be detected in many cases. (iii) Since the scattering of ultrasonic waves varies depending upon the shape and size of the flaw end, the measured values are not uniform and so the accuracy of measurement is low. (iv) Even if the ultrasonic waves are transmitted after being refracted through a nominal refraction angle of the probe toward the end of a flaw, no peak echo can be obtained in some cases, and when the beam center is not coincident with the end of the flaw, the peak echo is displayed in some cases. In such case, the basis for geometrical determination of the flaw depth is lost, directly causing the reduction of the accuracy of measurement.

As one of the conventional methods for measurement of the depth of a surface opening flaw, an invention by the Applicant is disclosed in Japanese Patent Application No. Sho 60-68379. The method disclosed in the Application a vertical type probe is placed on the surface of a solid mass possibly having an opening flaw therein and also just above the flaw and the propagation time of the scattered waves derived from the ultrasonic waves incident upon the end of the opening flaw through the reflection at the flaw end is measured to determine the depth of the flaw. Also in the method in said application, it is necessary, as in the afore-mentioned reports, to detect the echo from the surface opening flaw and the position thereof. As in the reports (2) and (3), the method is limited in various respects of measurement since it is necessary to place the probe just above the surface opening flaw for measurement of the depth of the flaw.

As has been described in the foregoing, in all the conventional methods of measuring the depth of a surface opening flaw, the echo from the end of the surface opening flaw and its position are taken as indices of measurement, so that the accuracy of measurement depends upon that of detection. Thus, it is necessary to improve the above-mentioned accuracy of detection. With surface opening flaws as well as ordinary internal flaws, however, the detection of an echo from a flaw and its position is seriously influenced by the properties of the material of the object under measurement, any difference in physical phenomenon of the ultrasonic wave due to the nonuniformity of the flaw, difference in skill from one operator to another, etc. even if a transducer is used, and the flaw detector and flaw detecting parameters such as flaw detecting sensitivity, etc. are maintained as predetermined for every measurement. So, even when objects of the same kind very similar to one another in shape, dimensions, material, etc. are measured, it is difficult to measure them always with the same accuracy. So, it is rather difficult to measure objects of different kinds with the same high accuracy. Therefore, the level of an echo from the end of a surface opening flaw existent in the object and its position cannot be so uniformly detected as in the detection of a surface opening flaw artificially formed in the standard test piece or an object even if the flaw depth is the same, and the accuracy of detection is correspondingly low.

OBJECTS AND BRIEF SUMMARY OF THE INVENTION

The present invention primarily seeks to overcome the above-mentioned drawbacks of the conventional techniques by providing an ultrasonic method of measuring the depth of a surface opening flaw in a solid mass, in which the depth of the surface opening flaw can be accurately and realtime measured without being influenced by the depth itself.

The present invention has as another object to provide an ultrasonic method for measurement of the depth of a surface opening flaw in a solid mass, in which an ordinary angle probe can be used to measure a wide range of objects in a wide technical field easily and accurately just by normally scanning the probe back and forth in relation to the flaw.

The above-mentioned objects can be attained by providing, according to the present invention, an ultrasonic method for measurement of the depth of any surface opening flaw possibly existent in a solid mass, comprising the steps of transmitting an ultrasonic wave into a solid mass undergoing flaw detection by scanning an ultrasonic angle probe back and forth on the surface of the solid mass with respect to a surface opening flaw in the solid mass; setting a threshold of a predetermined level for an envelope defined by echoes of the ultrasonic waves reflected from the surface opening flaw according to the moved position of the probe; integrating an area defined by the curve of the echo levels, i.e. the echo envelope and above the threshold for the range of movement of the angle probe within this area; and measuring the depth of the surface opening flaw taking as the evaluation index the value of the integrated area.

BRIEF DESCRIPTION OF THE DRAWINGS

Other advantages of the present invention will be better understood from the ensuing description, by way of example, of an embodiment with reference to the accompanying drawings, in which:

FIGS. 3(a) and 3(b) show an object made of welded steel plate to be measured in which a surface opening flaw is intentionally formed in the butt joint between the steel plates, FIG. 3(a) being a side elevation showing the object, and FIG. 3(b) being a plan view of the object;

FIGS. 11–13a, 13b show conventional typical methods of measuring the depth of a surface opening flaw, FIG. 11 being a schematic explanatory drawing showing the end peak echo method, FIG. 12 being an echo pattern obtained by the method shown in FIG. 11 and displayed on a CRT screen, and FIG. 13 being another example of measurement of a surface opening flaw by the end peak echo method.

DETAILED DESCRIPTION OF THE INVENTION

Figure 1:
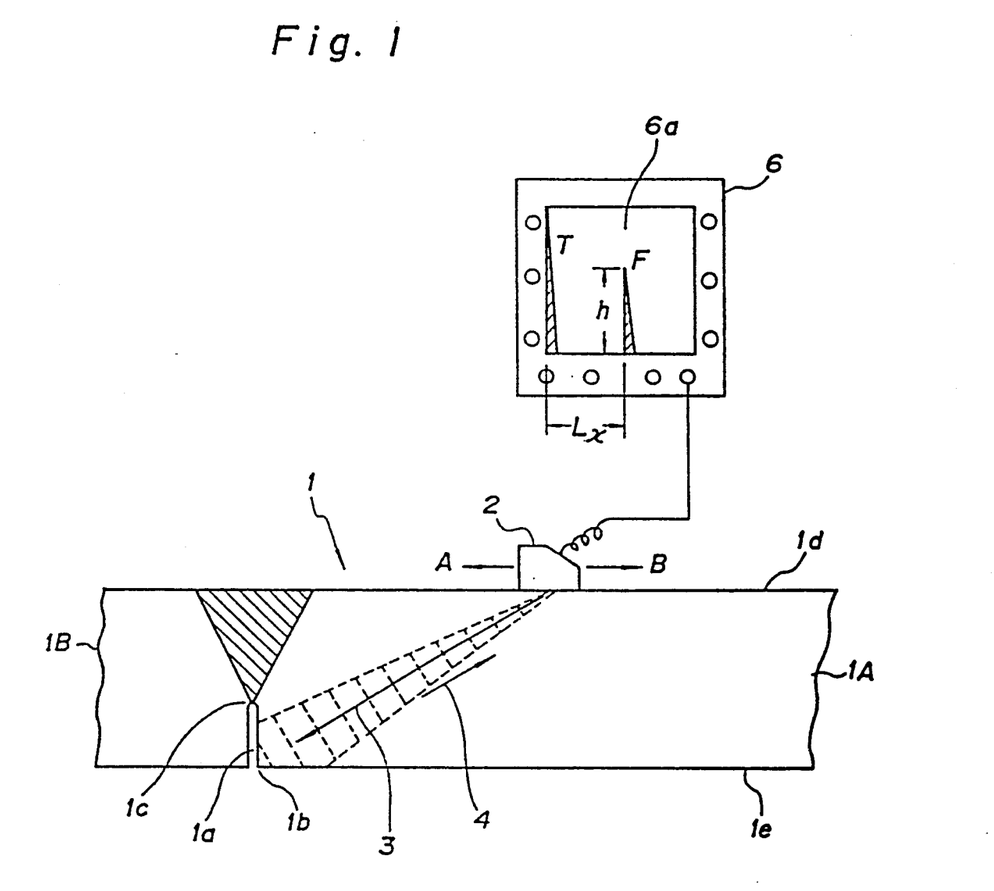
FIGS. 1 and 2a–b together show the principle of the ultrasonic method for measurement of a surface opening flaw according to the present invention, FIG. 1 showing the procedure for the measurement and FIG. 2 showing the formation of an echo envelope for the surface opening flaw.
Figure 2A:
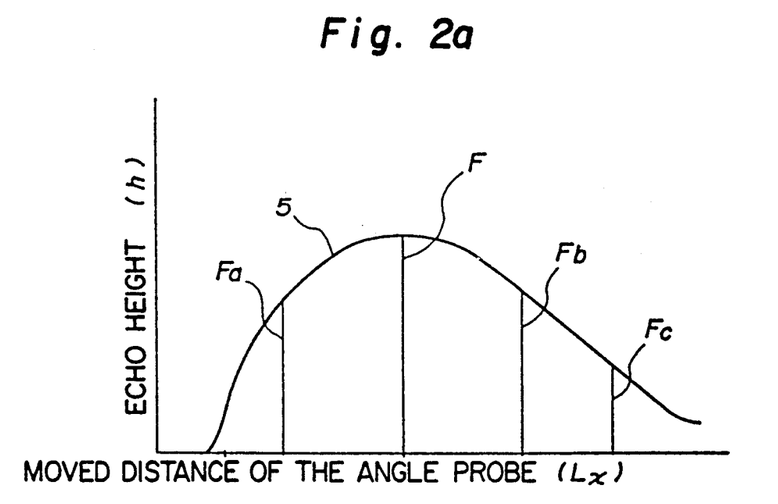
Figure 2B:
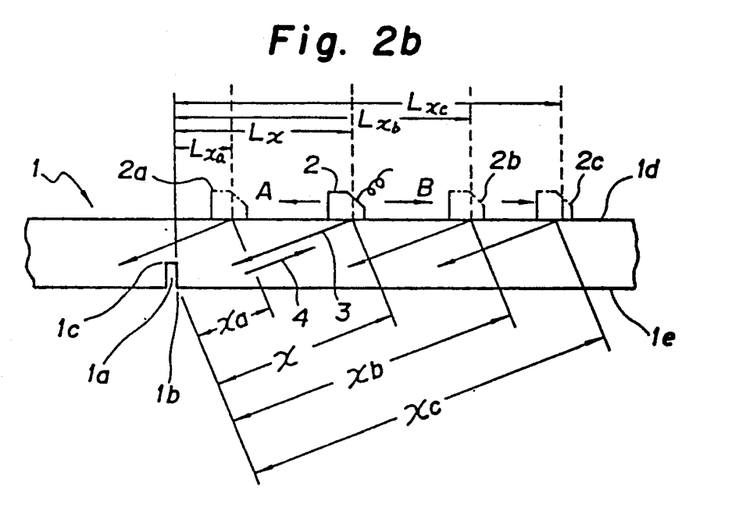

The present invention utilizes the fact that the value of the area determined by integrating the echoes-integrated zone above the predetermined echo level of the above-mentioned echo envelope for the range of movement in that zone of the angle probe is in a certain fixed relation with the depth of a surface opening flaw in a solid mass. This relation will be further explained with reference to FIGS. 1 and 2 showing the principle of the present invention.

In Figures, the reference number 1 indicates an object made, by butt-welding, of members 1A and 1B. A recess-like flaw 1a is included in the butt joint between these member 1A and 1B and it is opened to the side 1e of the object 1. The reference number 1b indicates a corner of the flaw 1a at the opening thereof, 1c the inner end of the flaw 1a and 1d a searching surface. The reference numeral 2 indicates an angle probe (will be referred to simply as a "probe" hereinafter) which is placed on the searching surface 1d. It is scanned back and forth to positions 2a, 2b, 2c, etc. each indicated with a dash line in the direction of arrow A or B on the object 1, and transmits an ultrasonic wave (transverse wave in this case) in the direction of the flaw 1a. The reference numeral 3 indicates an incident wave radiated within a predetermined beam width, and 4 a portion of the incident wave 3 that is reflected from the flaw 1a and received by the probe 2. When the reflected waves 4 received at various positions of the probe 2 such as the positions 2a, 2b, 2c, etc. as the probe 2 is scanned back and forth in relation to the flaw 1a are displayed on a CRT screen 6a of an ultrasonic flaw detector 6, they appear as echoes different in level from one another at positions corresponding to the moved positions of the probe 2 from the point at which a transmitted pulse T appears. FIG. 2 shows the relation between the probe positions and levels of echoes thus detected. As shown, there are displayed echoes F, $F_a$, $F_b$, $F_c$ of the reflected wave 4 at the positions on the CRT screen corresponding to the beam paths X, $X_a$, $X_b$, $X_c$ from the incidence points, namely, the positions 2, 2a, 2b and 2c of the probe 2, to the corner 1b of the flaw 1a at which the majority of the incident ultrasonic wave 3 is reflected. The horizontal axis in the plane of FIG. 2 indicates the horizontal distance ($L_x$ in mm) from the flaw 1a to the probe 2 while the vertical axis indicates the echo amplitude or height (h in dB). In this case, the echo corresponding to a position where the probe 2 receives the reflected wave 4 derived from the incident wave 3 of which the ultrasonic wave beam center is directly incident upon the corner 1b, that is, the echo F picked up at a position of a distance $L_x$ from the flaw 1a, has a maximum height, while the other echoes are different in level depending upon distances $L_{xa}$, $L_{xb}$ and $L_{xc}$, respectively, of the probe 2 from the flaw 1a and which are corresponding to the beam paths, respecttively. By connecting the echo peaks, an echo envelope 5 is obtained. Of course, when there is no flaw 1a in this case, no reflected waves are received and so an echo envelope 5 cannot be obtained.

The area beneath the echo envelope which appears on the CRT screen, namely, the area enclosed by the echo envelope 5 extending between one extreme end position of movement of the probe 2 and the other extreme end position, is a function of the "directivity of a transmitted wave depending upon the transducer dimensions of the probe used and the probe frequency", "directivity of reflected waves resulted from transmitted waves scattered and attenuated in a solid mass, when received by a probe" and "depth of surface opening flaw". Thus, when the same probe is used for the flaw detection, the directivity of transmission and reception is fixed, so that the zone on the CRT under the echo envelope 5 is a function of the "depth of surface opening flaw" alone. This means that when objects having different depths of surface opening flaws and which are the same in other respects are measured using the same probe, the resulting areas under the echo envelopes 5 have sizes depending upon the depth of the detected surface opening flaw and have analogous shapes.

The ultrasonic method of measuring the depth of surface opening flaw according to the present invention is such that a threshold of a predetermined echo level is set for the echo envelope having the aforementioned nature, and the area in which echo levels are above the threshold is integrated for a range movement of the probe in the area, and the depth of a surface opening flaw is measured based on the fact that the value of the integrated area is in a certain fixed correlation with the depth of the surface opening flaw. This correlation between the area of the integrated zone and the depth of surface opening flaw was proved by the Inventor of the present invention through experiments which will be described later, and can be easily determined, through similar experiments on solid mass of different materials as well. Also the echo envelope can be easily defined by echoes of the reflected waves from a surface opening flaw, which are displayed on the CRT screen, and a threshold can be arbitrarily set. So, as compared with the conventional methods for measuring the depth of surface opening flaw using the echo levels at certain positions, namely, the method for such measurement in which an unstable echo level at the end of a surface opening flaw and its displayed position are taken as evaluation indices, the method according to the present invention makes it possible to easily and accurately measure a wide variety of objects without being affected by the magnitude of the flaw depth, skills of the operator and other factors since it uses an area defined by an echo envelope always stably obtained by ordinarily scanning a commercially-available probe back and forth with respect to a possible surface opening flaw. This advantageous feature of the present invention also permits an easy implementation of an automatic measurement of a large quantity of objects.

In the foregoing, the measurement of the depth of a flaw opening from the surface of an object has been described, but the method of measurement according to the present invention can also be utilized for measurement of a flaw existent in an object very closely to the surface thereof even if the flaw is not open on the surface. The "flaw existent very closely to the surface of an object under measurement" refers to a flaw as to which the very short distance from the surface of the object is approximated to a distance which is likely to provide a reflecting spot similar to the corner 1b of the surface opening flaw 1a shown in FIG. 1. More particularly, that short distance is less than about a half of the wavelength depending upon the probe used and the material of the object under measurement. It is less than about 1 mm, for example. The flaw not open on any surface of the object and in the above-mentioned position provides an echo envelope when measured by a similar method to that for measurement of the aforementioned surface opening flaw, and can be measured similarly utilizing the idea on which the present invention is based.

BEST MODE FOR CARRYING OUT THE INVENTION

A preferred embodiment of the present invention will be described with reference to FIGS. 3 thru 10. In these Figures, the same elements as in FIGS. 1 and 2 are indicated with the same reference numerals.

Figure 3A:
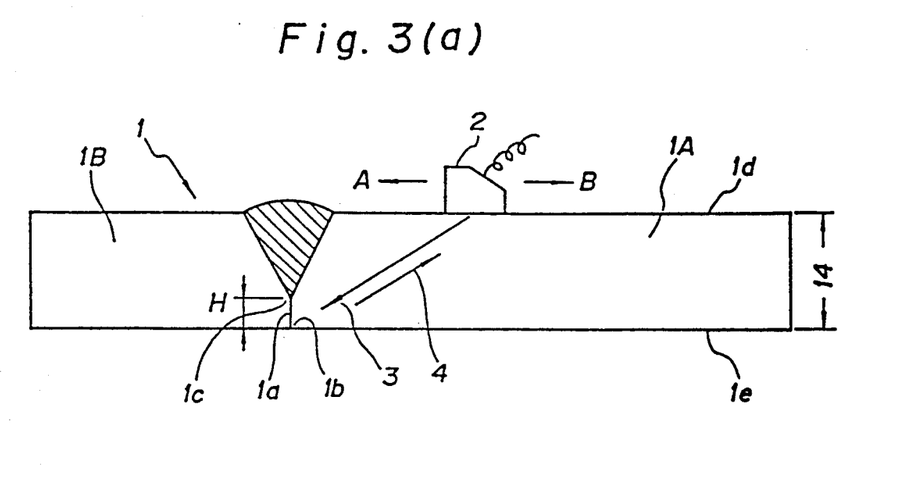
Figure 3B:
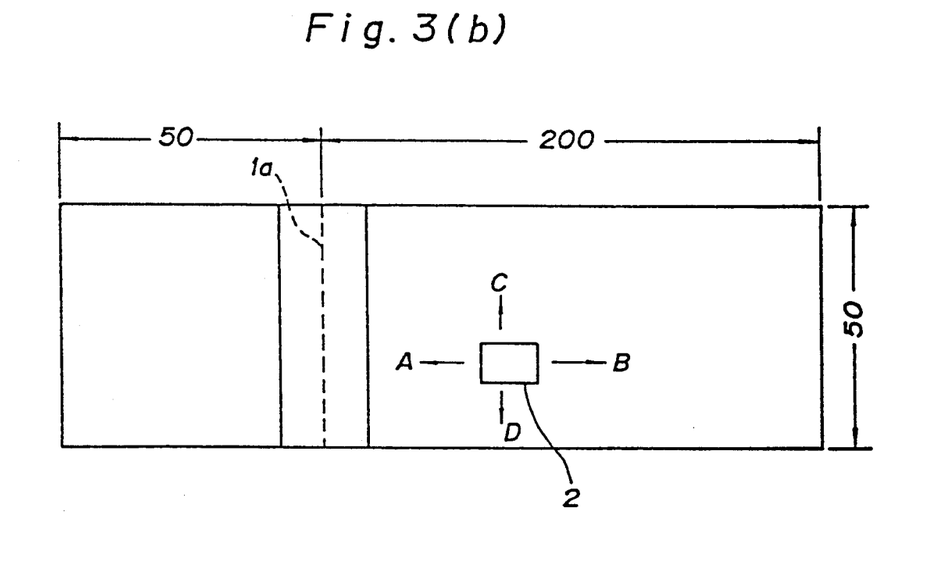

The shape and dimensions of the object 1 is shown in FIG. 3. FIG. 3 (a) is a side elevation of the object, while FIG. 3 (b) is a plan view. The object is formed from a member 1B of 14 mm in thickness, 50 mm in length and 50 mm in width and a member 1A of 14 mm in thickness, 200 mm in length and 50 mm in width, which are butt-welded to each other, and an open flaw 1a of a very narrow width and 0.1 to 10 mm in depth H is intentionally formed in the surface 1e of the above-mentioned butt joint. The material of the object is SS41 (JIS G3101) and seventeen samples were used in the Inventor's experiments. The probe 2 is 2Z10x10A70 (JIS Z2344) of 2 MHz frequency having dimensions of 10 mm $\times$ 10 mm and a refraction angle of 70 degrees.

Figure 4:
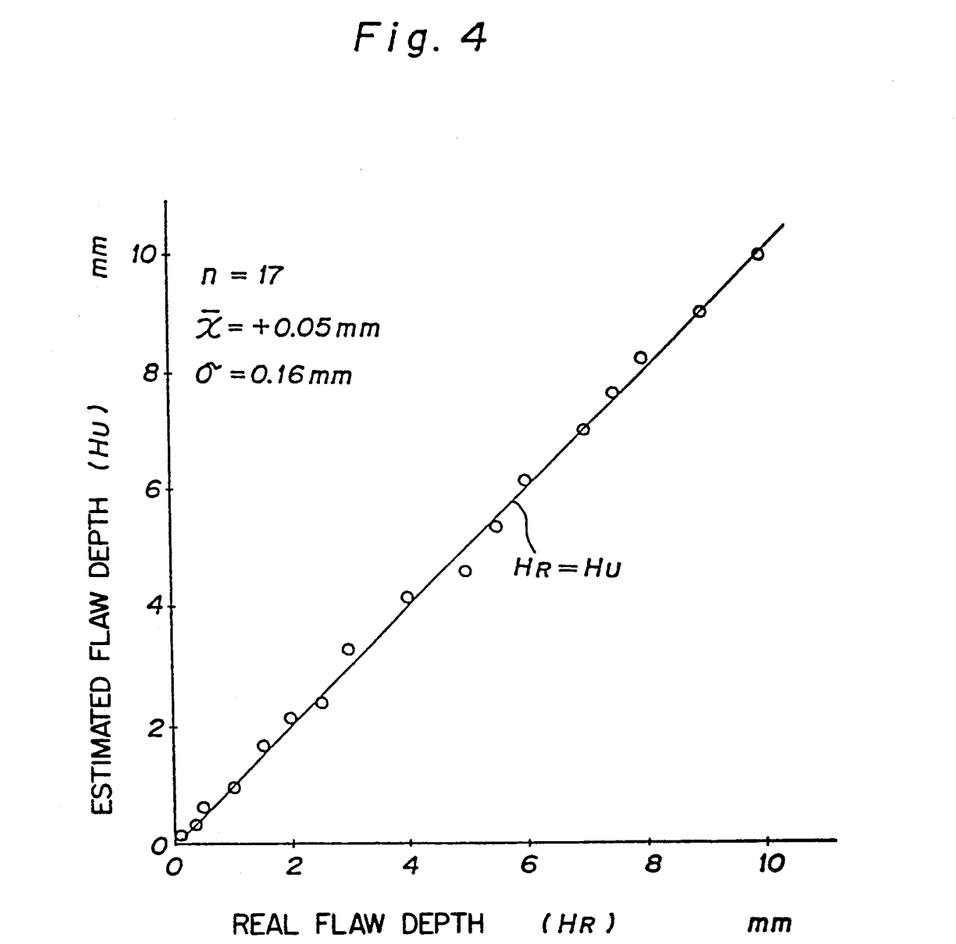
FIG. 4 graphically shows the relation between the estimated flaw depth as measured by the method shown in FIGS. 1 and 2 and the real flaw depth.

For the measurement of the depth of the flaw, the probe 2 was first placed on and in contact with the searching surface 1d and an echo envelope was obtained by the method previously explained with reference to FIGS. 1 and 2. Next, using a regression equation determined from the correlation, proved by the Inventor through his experiments, between the area of the above the predetermined echo level of the echo envelope and the depth of the surface opening flaw, various depths of the flaw 1a formed in the butt joint of the object 1 were measured. The measured values are shown with small circles in FIG. 4. For measurement of the depth H of the flaw H at another position in the longitudinal direction of the flaw, namely, in the direction of the width of the object 1, the probe 2 was successively moved in the direction of arrow C or D in FIG. 3 and then scanned back and forth in relation to the flaw 1a. After completion of the scan in all the intended directions, the object 1 was cut and micro-etched, and the real depth of the flaw 1a was measured using a 20X magnifier. In FIG. 4, the horizontal axis indicates the values $H_R$ (in mm) of the real flaw depth measured with the object 1 cut and the vertical axis indicates the value $H_U$ (in mm) of the estimated flaw depth measured by the method according to the present invention. Also in FIG. 4, the solid line (slanted at 45 deg.) indicates that the real measured value $H_R$ is equal to the estimated value $H_U$, namely, the measurement error is zero. As seen from FIG. 4, the small circles for the measured values are all very close to the solid line. The mean value (x) and standard deviation ($\sigma$) of the measurement errors in this embodiment are determined as follows:

x = +0.05 mm $\sigma$ = 0.16 mm

Namely, this high accuracy of measurement is not affected by the depth H of the flaw 1a and it is also proved that the method of measurement according to the present invention is excellent in accuracy of measurement. This high accuracy is due to the utilization of the principle that the echo envelopes derived from different depths H of the surface opening flaws are analogous to each other although having a different echo level so long as the same probe is used in the measurements and that the objects measured are the same in shape, dimensions and material. Because accuracy of measurement is not affected by the magnitude of the depth H of the flaw 1a, this allows the measurement of micro flaws.

Figure 5A:
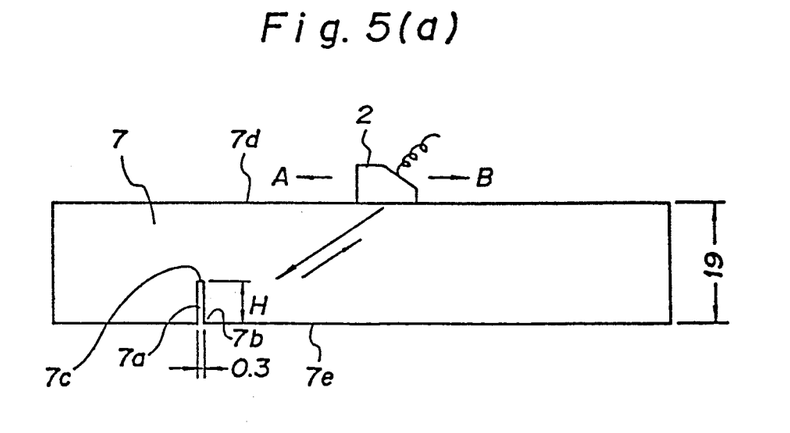
FIGS. 5(a) and 5(b) show a test piece used in the inventor's experiments to prove the effect of the present invention, FIG. 5(a) being a side elevation of the test piece and FIG. 5(b) being a plan view of the test piece.
Figure 5B:
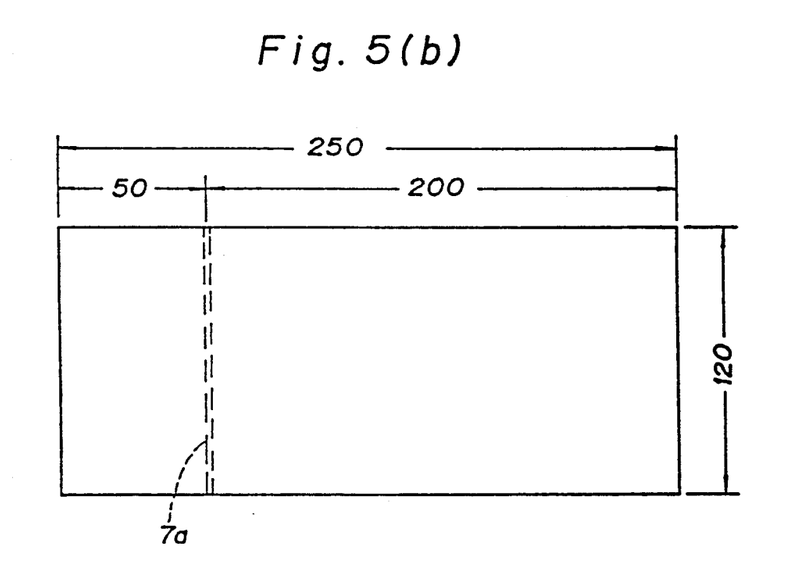
Figure 6:
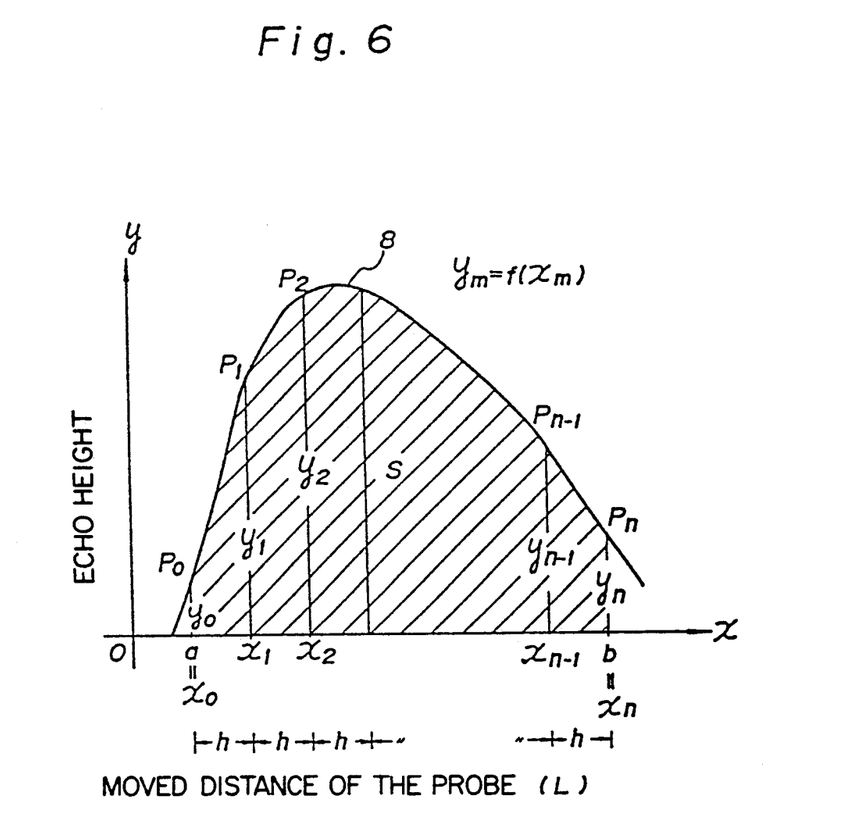
FIG. 6 is an explanatory drawing shown the determination by the Simpson's rule of the area of the range of probe movement defined by an echo envelope.

The aforementioned effect of the present invention was proved by the Inventor of the present invention through his experiments which will be described below:

FIG. 5 shows a test sample measured by the method according to the present invention; FIG. 5 (a) is a side elevation of the test sample, and FIG. 5 (b) is a plan view of the test sample. The test sample 7 was a steel plate (SS41, JIS G3101) of 19 mm in thickness, 250 mm in length and 120 mm in width, in which a slit 7a of 0.3 mm in width was intentionally formed by an electric discharge machining in the surface 7e at a position 50 mm away from, one end of the test sample 7. The slit 7a had eight depths H (0.3, 0.5, 1.0, 2.0, 3.0, 4.0, 5.0 and 7.0 mm). The probe used was the same one (2Z10×10A70 according to JIS Z2344) as in the explanation given with reference to FIG. 3. By placing this probe on and in contact with the searching surface 7d and scanning it back and forth in relation to the slit 7a while transmitting ultrasonic waves toward the slit 7a, an echo envelope 8 shown in FIG. 6 was obtained as in the explanation previously made with reference to FIGS. 1 and 2. Next, the area under the echo envelope 8 was measured. In this experiment, however, the threshold for the predetermined level of the echo was set as the flaw-detection sensitivity (set to 0 dB) for one-skip distance of the hole of 4 dia. ×4 in the "Type A2 sensitivity calibration test sample for ultrasonic flaw detection with oblique radiation (will be referred to as "STB-A2" hereinafter)" in JIS Z2348 (1978) and the area defined by the curve of the echo levels above this threshold was determined. For determination of this area, the following Simpson's rule was used assuming that the distance of movement of the probe for the echo envelope 8 in FIG. 6, namely, the integrated range of the area (a, b) to be determined, was divided into n equal sections having a width $h=(b-a)/n$ (n is an even number), $x_m=a+mh$ (m=0, 1, 2, ... ) and that the equation for the echo envelope 8 was $y_m=f(x_m)$:

$$S = \int_a^b f(x)dx = \{y_0 + y_n + 4 \ (y_1 + y_3 + \ldots + y_{n-1}) + 2(y_2 + y_4 + \ldots y_{n-2})\}h/3$$

The area indicated as hatched in FIG. 6 is the intended area, and $P_0, P_1, P_2, \ldots P_n$ indicate echo levels for the one-skip distance at the equally-divided positions.

Figure 7:
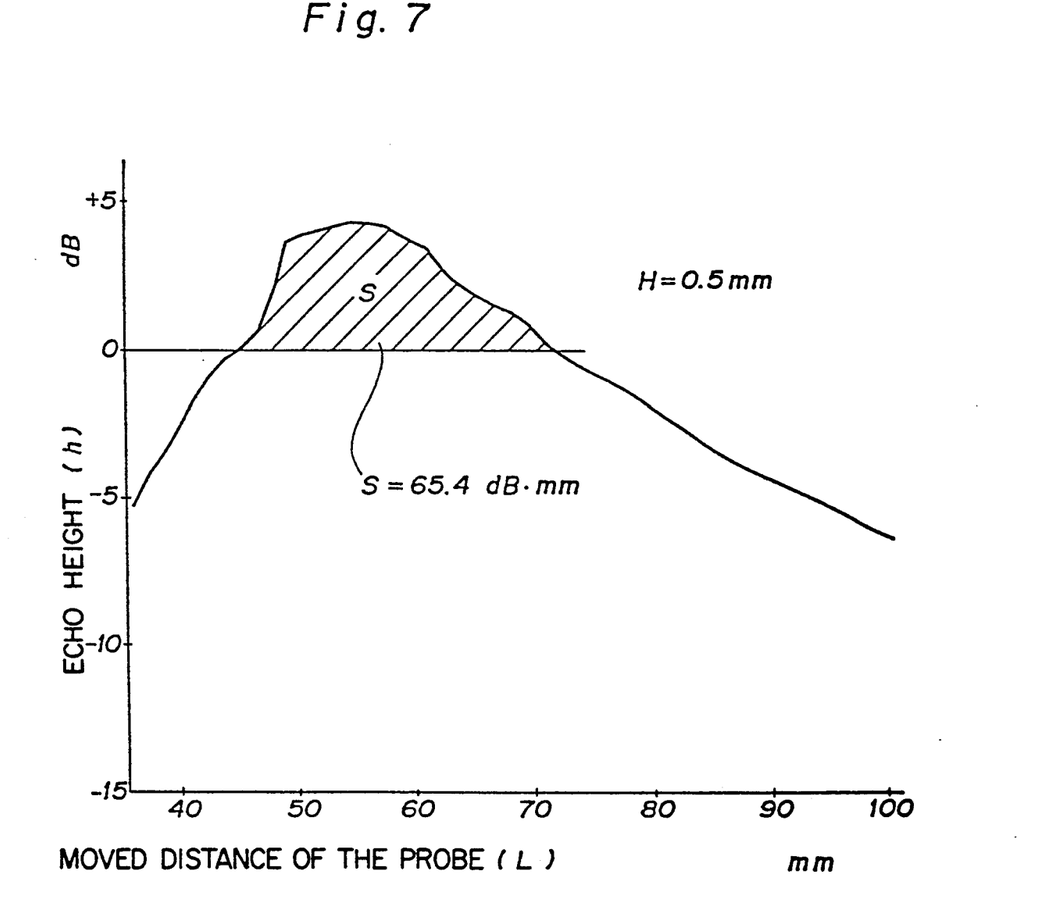
FIGs. 7–9 show the results of experiments conducted on three kinds of test pieces of the type shown in FIG. 5 and which have different depths of slits therein.
Figure 8:
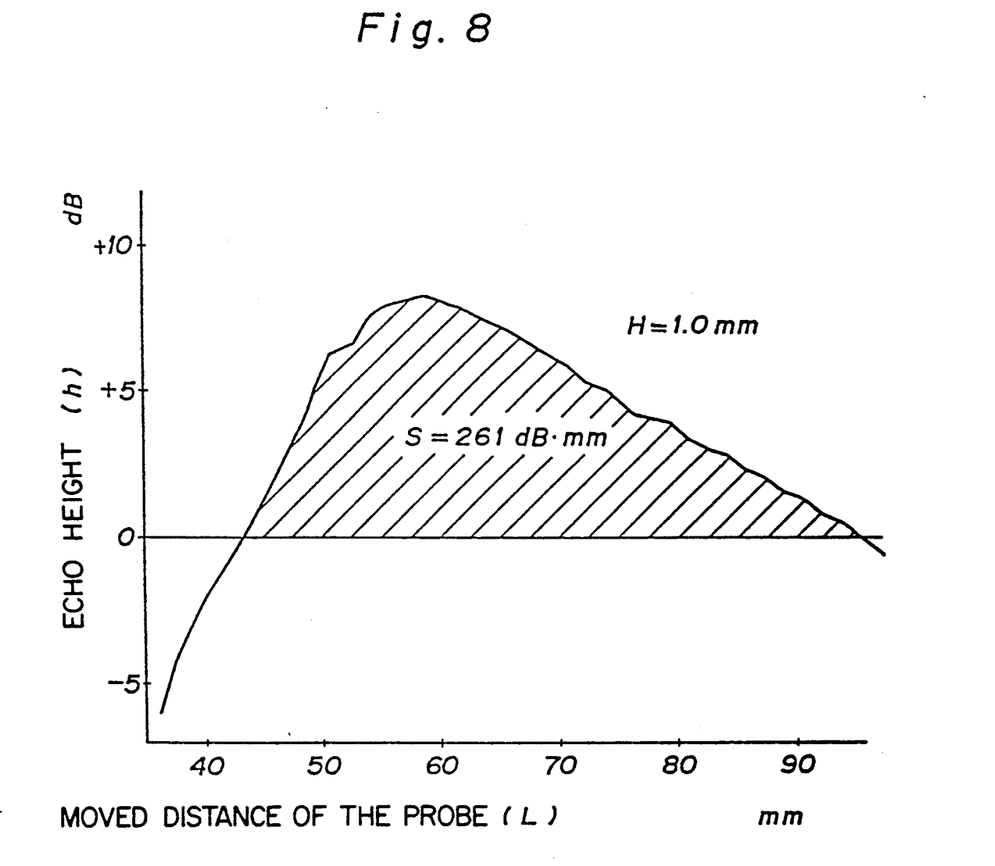
Figure 9:
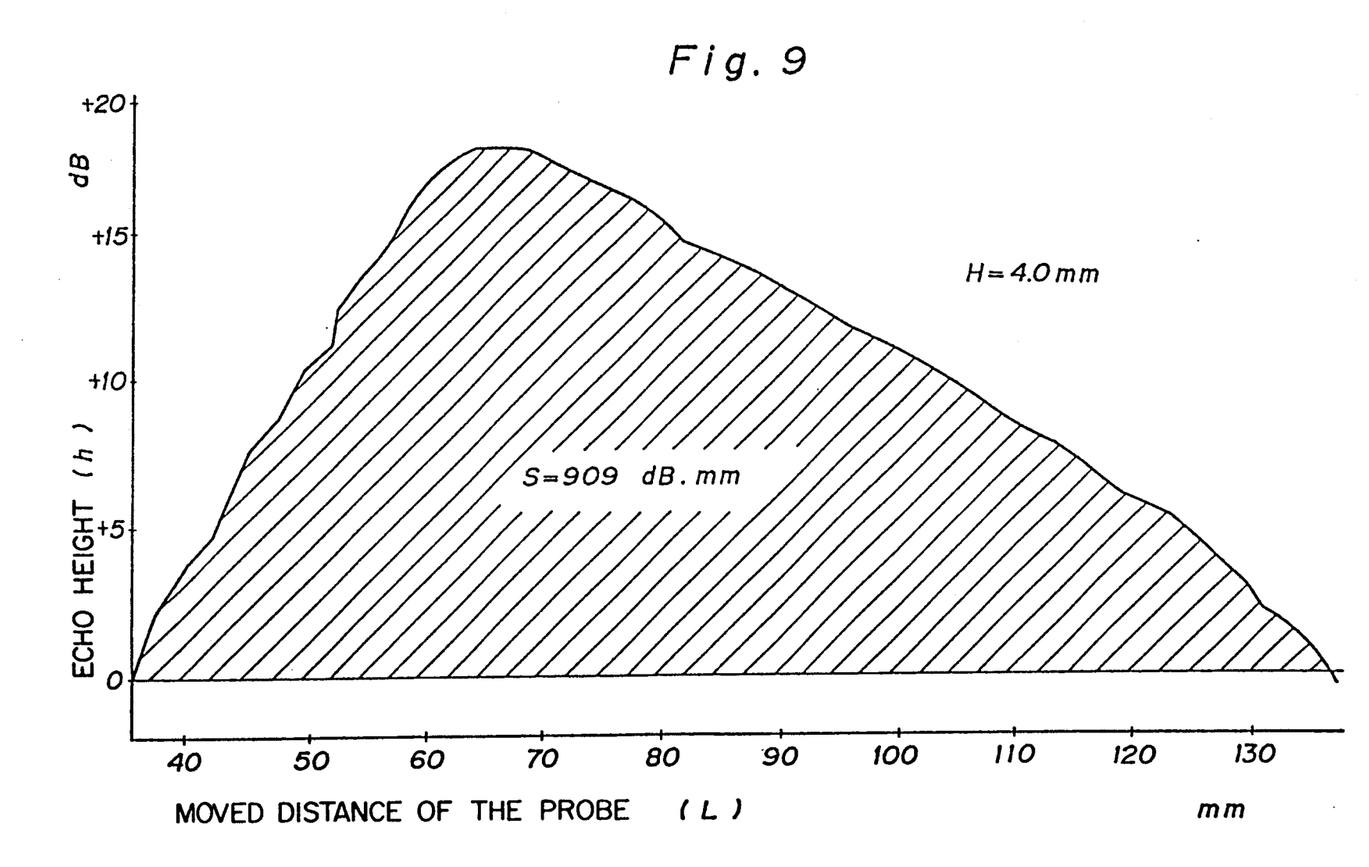
Figure 10:
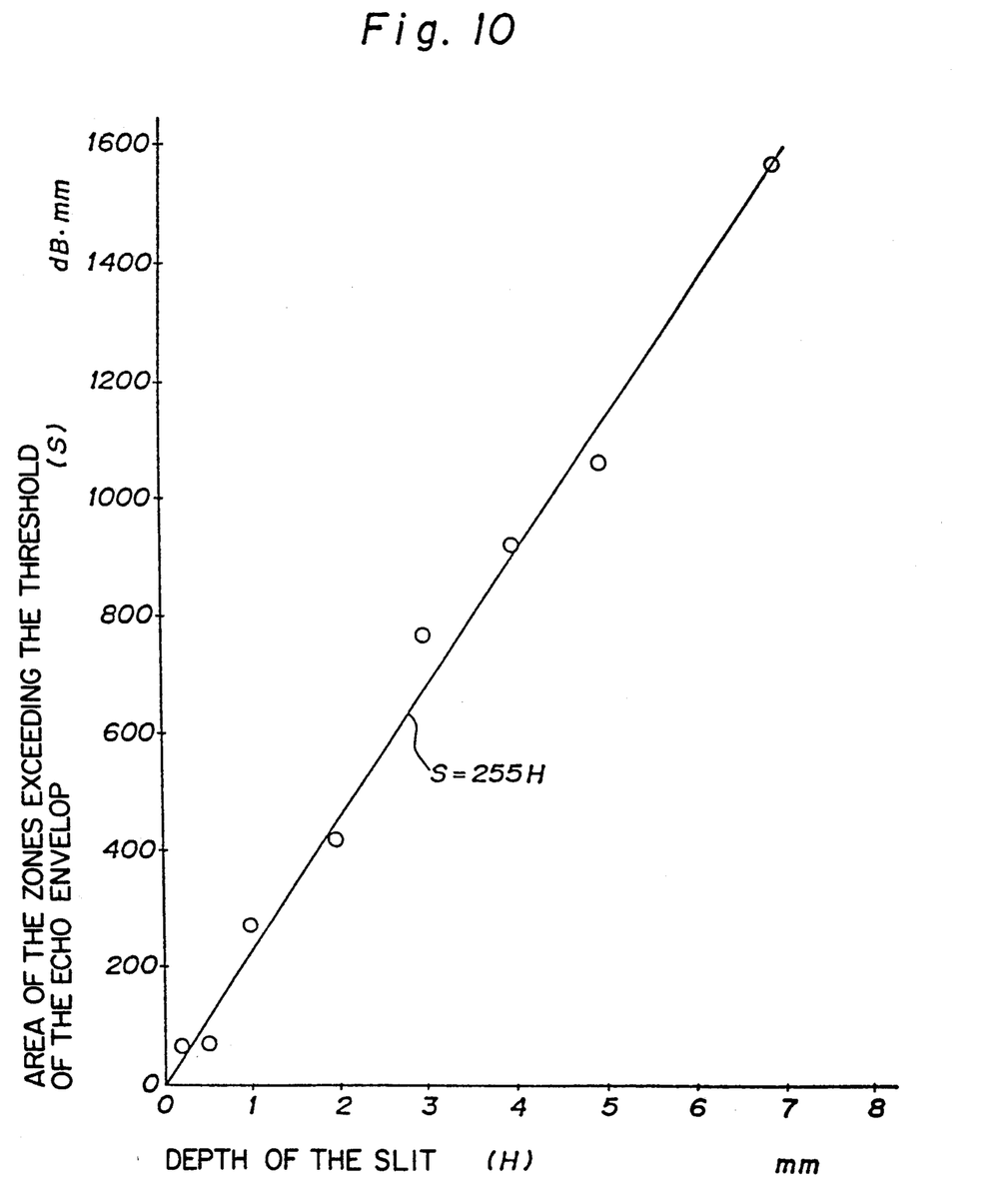
FIG. 10 is an explanatory drawing showing the correlation between the slit depth of the test piece shown in FIG. 5 and the area of the echo envelope above the threshold.

The results of the experiments conducted on the above-mentioned test sample 7 are described with reference to FIGS. 7 thru 9 for three examples, respectively, of the depth 7 of the slit 7a (H=0.5, 1.0 and 4.0 mm). In each of Figures, the horizontal axis indicates the distance L of movement of the probe (probe-flaw distance) and the vertical axis indicates the echo level h. The threshold is the sensitivity (0 dB) for the one-skip distance of the STB-A2. First, FIG. 7 shows the result of the experiment on the depth H of the slit 7a being 0.5 mm. The area S of the zone above the threshold of 0 dB, indicated with a letter S, was calculated to be 65.4 dB.mm from the Simpson's rule. FIG. 8 shows the result of the experiment on the depth H of 1.0 mm. The area S is calculated to be 261 dB.mm. FIG. 9 shows the result of the experiment conducted on the depth H=4.0 mm. The area S is calculated to be 909 dB.mm. As obvious from these three example experiment results, the larger the depth H of the slit 7a, the larger the maximum echo level becomes and the larger the area S of the zone above the threshold is. This correlation will be more definitely shown in FIG. 10 showing the relation between the area S determined on the above-mentioned eight kinds of test samples and the depths H of the slit 7a. The horizontal axis indicates the depth H of the slit (in mm) while the vertical axis indicates the areas S (in dB.mm) of zones above the threshold of the echo envelope. The small circles in the Figure indicate the experimental results of the eight test samples. The results show that a linear correlation is established between the slit depth H and area value S. Using the method of least squares, the following simple regression equation of of the graph can be obtained:

$$S = 255H$$

It was proved that using this equation, it is possible to easily determine the flaw depth from the area of a zone above the threshold and under the echo envelope and accurately measure the depth from the linear correlation without being affected by the magnitude of the flaw depth.

Example measurements of flaw depth with the probe placed in contact with the surface at the side of an object at which no surface opening flaw exists have been explained with reference to FIGS. 1 thru 3 and 5, but the present invention is not limited to such method of measurement. The probe may be scanned back and forth in contact with the surface on the side of the object in which any surface opening flaw exists. In this case, however, the probe is to be placed at a position where the incident wave transmitted from the probe into the object reaches the surface opening flaw after being reflected at the rear side of the object, namely, at a position nearly one skip distance from the surface opening flaw, and the probe is scanned back and forth with respect to the one skip distance position. The sensitivity of the ultrasonic flaw detector is to be adjusted for the corresponding increment of the beam path.

The above-described echo envelope varies in shape and dB value depending on the acoustic characteristics of the material of the object, angle of inclination formed between the surface opening flaw and the object surface and other similar factors. So, by determining, through experiments, the echo envelopes of solid masses of various kinds with the angle of inclination changed variously beforehand, it is possible to measure the depth of a surface opening flaw simply, easily and accurately as in the aforementioned embodiment. This simplicity and easiness of measurement assured by the present invention effectively provides a realtime flaw-depth measurement of a wide variety of objects in a wide range.

The method having been described in the foregoing is a one in which an echo displayed on the CRT screen is to be visually observed. Also, it is possible to digitize an analogue quantity of echo levels defining together an echo envelope by a well-known means without displaying the echo on the CRT screen, calculate the area defined by the echo envelope in an area above a threshold and display in a digital form the calculated area along with the depth of surface opening flaw calculated using a regression equation. Further, these values can be stored in a memory and compared with a reference value to diagnose a machine for any trouble or for its remaining service life, and can be used for automatic measurement of a great number of objects in a production line.

Of course, the present invention is not limited to the embodiment having been described in the foregoing, but can be provided in various many forms without departing from the scope and spirit set forth in the claims.

What is claimed is:

1. A method for ultrasonic measurement of the depth of a surface opening flaw which may be present in a solid mass, comprising the steps of:

scanning an ultrasonic probe which emits an ultrasonic wave at a wave angle back and forth on a surface of the solid mass toward and away from a position of a suspected surface opening flaw in the solid mass for transmitting an ultrasonic wave into the solid mass;

forming values of the echoes of the ultrasonic wave reflected from the surface opening flaw at the different positions of movement of said probe and which are above a predetermined level into a curve of the echo levels above said predetermined level and at said probe positions;

integrating the area beneath said curve and above said predetermined level for the range of movement of said probe; and using the value of said integrated areas as an evaluation index for determining the depth of said surface opening flaw.

2. The method according to claim 1 wherein the solid mass has a first surface in which the suspected surface opening flaw is present and a second surface other than said first surface, and said probe is placed on and in contact with said second surface and scanned on said second surface.

3. The method according to claim 1 wherein said solid mass has a first surface in which the suspected surface flaw is present and a second surface parallel to said first surface, and said probe is placed on and in contact with said first surface at a position about one skip distance from the position of the suspected surface flaw and scanned toward and away from the position of the suspected surface opening flaw about the one skip distance position.

4. The method according to claim 1 wherein said predetermined level corresponds to a flaw-detection sensitivity of said probe of a one skip distance of a sensitivity standard test sample.

* * * * *